(12) United States Patent
O'Prey et al.

(10) Patent No.: US 8,585,712 B2
(45) Date of Patent: Nov. 19, 2013

(54) SURGICAL RETRIEVAL APPARATUS

(75) Inventors: Cormac O'Prey, Bishops Stortford (GB); Alistair Ian Fleming, Lower Cambourne (GB); Michael J. Bettuchi, Middletown, CT (US); Iain Ansell, Newmarket (GB)

(73) Assignee: Covidien LP, Mansfield, MA (US)

( * ) Notice: Subject to any disclaimer, the term of this patent is extended or adjusted under 35 U.S.C. 154(b) by 447 days.

(21) Appl. No.: 12/969,679

(22) Filed: Dec. 16, 2010

(65) Prior Publication Data

US 2011/0190780 A1  Aug. 4, 2011

Related U.S. Application Data

(60) Provisional application No. 61/301,105, filed on Feb. 3, 2010.

(51) Int. Cl.
*A61B 17/22* (2006.01)

(52) U.S. Cl.
USPC ......................................................... 606/114

(58) Field of Classification Search
USPC ................ 606/110–115, 127, 128, 106, 200; 600/562, 564–567; 604/59–64, 604/327–328
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,927,427 A | 5/1990 | Kriauciunas et al. |
| 4,997,435 A | 3/1991 | Demeter |
| 5,037,379 A * | 8/1991 | Clayman et al. ................ 600/37 |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |

(Continued)

FOREIGN PATENT DOCUMENTS

| | | |
|---|---|---|
| DE | 8435489 | 12/1984 |
| DE | 3542667 | 6/1986 |

(Continued)

*Primary Examiner* — Kathleen Holwerda
*Assistant Examiner* — Rachel S Papeika

(57) ABSTRACT

A method of retrieving a tissue specimen comprising inserting a surgical retrieval apparatus through an opening in a patient's skin, the surgical retrieval apparatus including a support member and a retrieval bag extending from the support member and having an opening to receive the tissue specimen. A net is introduced into the retrieval bag and placed over the tissue specimen. The net and retrieval bag are removed from the patient's body to remove the tissue specimen.

16 Claims, 8 Drawing Sheets

(56) References Cited

U.S. PATENT DOCUMENTS

| | | | |
|---|---|---|---|
| 5,215,521 A | 6/1993 | Cochran et al. | |
| 5,234,439 A | 8/1993 | Wilk et al. | |
| 5,279,539 A | 1/1994 | Bohan et al. | |
| 5,312,416 A | 5/1994 | Spaeth et al. | |
| 5,330,483 A | 7/1994 | Heaven et al. | |
| 5,336,227 A | 8/1994 | Nakao et al. | |
| 5,337,754 A | 8/1994 | Heaven et al. | |
| 5,341,815 A | 8/1994 | Cofone et al. | |
| 5,352,184 A | 10/1994 | Goldberg et al. | |
| 5,354,303 A | 10/1994 | Spaeth et al. | |
| 5,368,545 A | 11/1994 | Schaller et al. | |
| 5,368,597 A | 11/1994 | Pagedas | |
| 5,370,647 A | 12/1994 | Graber et al. | |
| 5,465,731 A | 11/1995 | Bell et al. | |
| 5,480,404 A | 1/1996 | Kammerer et al. | |
| 5,486,183 A | 1/1996 | Middleman et al. | |
| 5,499,988 A | 3/1996 | Espiner et al. | |
| 5,524,633 A | 6/1996 | Heaven et al. | |
| 5,535,759 A | 7/1996 | Wilk | |
| 5,611,803 A | 3/1997 | Heaven et al. | |
| 5,618,296 A | 4/1997 | Sorensen et al. | |
| 5,630,822 A | 5/1997 | Hermann et al. | |
| 5,643,282 A * | 7/1997 | Kieturakis | 606/114 |
| 5,643,283 A | 7/1997 | Younker | |
| 5,645,083 A | 7/1997 | Essig et al. | |
| 5,647,372 A * | 7/1997 | Tovey et al. | 600/562 |
| 5,649,902 A | 7/1997 | Yoon | |
| 5,658,296 A | 8/1997 | Bates et al. | |
| 5,679,423 A | 10/1997 | Shah | |
| 5,735,289 A * | 4/1998 | Pfeffer et al. | 600/564 |
| 5,755,724 A | 5/1998 | Yoon | |
| 5,759,187 A | 6/1998 | Nakao et al. | |
| 5,769,794 A | 6/1998 | Conlan et al. | |
| 5,785,677 A | 7/1998 | Auweiler | |
| 5,788,709 A | 8/1998 | Riek et al. | |
| 5,792,145 A | 8/1998 | Bates et al. | |
| 5,814,044 A | 9/1998 | Hooven | |
| 5,836,953 A | 11/1998 | Yoon | |
| 5,853,374 A | 12/1998 | Hart et al. | |
| 5,895,392 A | 4/1999 | Riek et al. | |
| 5,906,621 A | 5/1999 | Secrest et al. | |
| 5,957,884 A | 9/1999 | Hooven | |
| 5,971,995 A | 10/1999 | Rousseau | |
| 5,980,544 A | 11/1999 | Vaitekunas | |
| 5,997,547 A | 12/1999 | Nakao et al. | |
| 6,004,330 A | 12/1999 | Middleman et al. | |
| 6,007,512 A | 12/1999 | Hooven | |
| 6,019,770 A | 2/2000 | Christoudias | |
| 6,036,681 A | 3/2000 | Hooven | |
| 6,059,793 A | 5/2000 | Pagedas | |
| 6,123,701 A | 9/2000 | Nezhat | |
| 6,152,932 A | 11/2000 | Ternström | |
| 6,162,235 A | 12/2000 | Vaitekunas | |
| 6,165,121 A | 12/2000 | Alferness | |
| 6,168,603 B1 | 1/2001 | Leslie et al. | |
| 6,228,095 B1 | 5/2001 | Dennis | |
| 6,270,505 B1 | 8/2001 | Yoshida et al. | |
| 6,277,083 B1 | 8/2001 | Eggers et al. | |
| 6,280,450 B1 | 8/2001 | McGuckin, Jr. | |
| 6,344,026 B1 | 2/2002 | Burbank et al. | |
| 6,348,056 B1 | 2/2002 | Bates et al. | |
| 6,350,266 B1 | 2/2002 | White et al. | |
| 6,350,267 B1 | 2/2002 | Stefanchik | |
| 6,383,195 B1 | 5/2002 | Richard | |
| 6,383,196 B1 | 5/2002 | Leslie et al. | |
| 6,383,197 B1 | 5/2002 | Conlon et al. | |
| 6,406,440 B1 | 6/2002 | Stefanchik | |
| 6,409,733 B1 | 6/2002 | Conlon et al. | |
| 6,419,639 B2 | 7/2002 | Walther et al. | |
| 6,447,523 B1 | 9/2002 | Middleman et al. | |
| 6,471,659 B2 | 10/2002 | Eggers et al. | |
| 6,506,166 B1 | 1/2003 | Hendler et al. | |
| 6,508,773 B2 | 1/2003 | Burbank et al. | |
| 6,530,923 B1 * | 3/2003 | Dubrul et al. | 606/45 |
| 6,537,273 B1 | 3/2003 | Sosiak et al. | |
| 6,589,252 B2 | 7/2003 | McGuckin, Jr. | |
| 6,752,811 B2 | 6/2004 | Chu et al. | |
| 6,755,779 B2 | 6/2004 | Vanden Hoek et al. | |
| 6,780,193 B2 | 8/2004 | Leslie et al. | |
| 6,805,699 B2 | 10/2004 | Shimm | |
| 6,840,948 B2 | 1/2005 | Albrecht et al. | |
| 6,872,211 B2 | 3/2005 | White et al. | |
| 6,887,255 B2 | 5/2005 | Shimm | |
| 6,994,696 B2 | 2/2006 | Suga | |
| 7,052,454 B2 | 5/2006 | Taylor | |
| 7,052,501 B2 | 5/2006 | McGuckin, Jr. | |
| 7,090,637 B2 | 8/2006 | Danitz et al. | |
| 7,270,663 B2 | 9/2007 | Nakao | |
| 7,273,488 B2 | 9/2007 | Nakamura et al. | |
| 7,410,491 B2 | 8/2008 | Hopkins et al. | |
| 7,547,310 B2 | 6/2009 | Whitfield | |
| 7,618,437 B2 * | 11/2009 | Nakao | 606/213 |
| 2004/0097960 A1 | 5/2004 | Terachi et al. | |
| 2005/0267492 A1 | 12/2005 | Poncet et al. | |
| 2006/0052799 A1 | 3/2006 | Middleman et al. | |
| 2006/0058776 A1 | 3/2006 | Bilsbury | |
| 2006/0200169 A1 | 9/2006 | Sniffin | |
| 2006/0200170 A1 | 9/2006 | Aranyi | |
| 2006/0229639 A1 | 10/2006 | Whitfield | |
| 2006/0229640 A1 | 10/2006 | Whitfield | |
| 2007/0016224 A1 | 1/2007 | Nakao | |
| 2007/0016225 A1 | 1/2007 | Nakao | |
| 2007/0073251 A1 | 3/2007 | Zhou et al. | |
| 2007/0088370 A1 | 4/2007 | Kahle et al. | |
| 2007/0135780 A1 | 6/2007 | Pagedas | |
| 2007/0135781 A1 | 6/2007 | Hart | |
| 2008/0082516 A1 * | 4/2008 | Niina | 707/4 |
| 2008/0188766 A1 | 8/2008 | Gertner | |
| 2008/0221588 A1 | 9/2008 | Hollis et al. | |
| 2008/0221604 A1 * | 9/2008 | Kondoh et al. | 606/170 |
| 2008/0234696 A1 | 9/2008 | Taylor et al. | |
| 2008/0300621 A1 | 12/2008 | Hopkins et al. | |
| 2008/0312496 A1 | 12/2008 | Zwolinski | |
| 2009/0082779 A1 | 3/2009 | Nakao | |
| 2009/0182292 A1 | 7/2009 | Egle et al. | |
| 2009/0192510 A1 | 7/2009 | Bahney | |
| 2009/0240238 A1 | 9/2009 | Grodrian et al. | |
| 2010/0000471 A1 | 1/2010 | Hibbard | |

FOREIGN PATENT DOCUMENTS

| | | |
|---|---|---|
| FR | 1272412 | 9/1961 |
| WO | WO 93/15675 | 8/1993 |
| WO | WO 95/09666 | 4/1995 |
| WO | WO 2004/002334 A1 | 1/2004 |
| WO | WO 2005/0112783 A1 | 12/2005 |

* cited by examiner

FIG_1

FIG_2

FIG_3

FIG_4

FIG_5

FIG_6

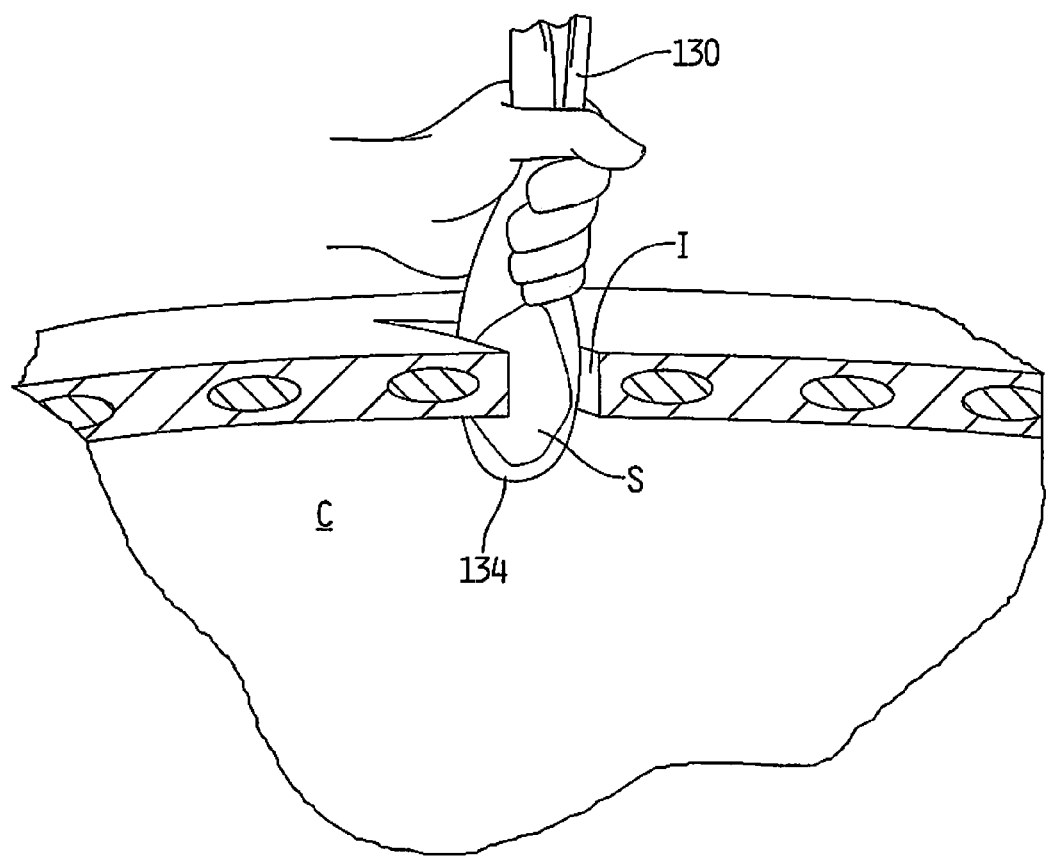
FIG_8

SURGICAL RETRIEVAL APPARATUS

This application claims priority from provisional application Ser. No. 61/301,105, filed Feb. 3, 2010, the entire contents of which are incorporated herein by reference.

BACKGROUND

1. Technical Field

The present disclosure relates to a surgical containment apparatus. More particularly, the present disclosure relates to a specimen retrieval apparatus for use in minimally invasive surgical procedures.

2. Background of Related Art

In minimally invasive surgical procedures operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, laparoscopic and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to prevent seeding of cancer cells.

In minimally invasive thoracic surgery, access to the thoracic cavity is limited as well as maneuverability within the cavity as the access port is placed between the confined space between a patient's ribs. Such procedures, commonly referred to as video assisted thoracoscopic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thoracoscopic wedge resection and lobectomy, it is often necessary to remove a portion of the lung and retrieve it relatively intact for pathology. It is also important that the specimen be sufficiently contained to prevent seeding of cancer cells during manipulation and removal.

In designing such specimen retrieval instrumentation, a balance must be struck between the need to provide a retrieval apparatus with a strong enough containment bag to prevent tearing or rupture while providing sufficient rigidity to enable manipulation and removal. Another balance which needs to be achieved is to provide sufficient maneuverability while reducing tissue trauma, e.g. damaging lung tissue, during manipulation and removal. Additionally, the instrumentation on one hand should be able to be inserted through a small access incision or port while on the other hand be able to accommodate a wide range of patient sizes and be able to easily remove large specimens and minimize risk of seeding.

It would therefore be advantageous to provide a specimen retrieval device for minimally invasive surgical procedures with increased maneuverability and which minimizes trauma to surrounding tissue and which successfully achieves the balance of competing factors enumerated above.

SUMMARY

The present disclosure is directed to a surgical retrieval apparatus. The present disclosure provides in one aspect a method of retrieving a tissue specimen comprising:

a) inserting a surgical retrieval apparatus through an opening in a patient's skin, the surgical retrieval apparatus including:

a support member, and a retrieval bag extending from the support member and having an opening to receive the tissue specimen;

b) placing a net over the tissue specimen; and c) removing the net and retrieval bag from the patient's body to remove the tissue specimen.

The method preferably further comprises the step of introducing the net into the retrieval bag. This step in a preferred embodiment occurs before the step of placing the net over the tissue specimen.

In a preferred embodiment, the net is introduced into the retrieval bag by a grasper with the net positioned on a shaft of the grasper. The method can include the step of unrolling the net from a shaft of the grasper.

The method may further include the step of advancing a second grasper through a second opening in the patient's skin into the retrieval bag and grasping the net with the second grasper.

In a preferred embodiment, the retrieval bag is positioned within a body cavity with an opening of the bag facing transversely with respect to the incision. A second grasper can be inserted through the transversely positioned opening.

The net preferably has a diameter less than the diameter of the tissue specimen to grip the tissue sample and maintain its position during removal.

In some embodiments, the step of inserting the surgical apparatus includes the step of inserting the apparatus into the thoracic cavity.

BRIEF DESCRIPTION OF THE DRAWINGS

Embodiments of the presently disclosed specimen retrieval apparatus are described hereinbelow with reference to the drawings wherein:

FIG. 8 is a perspective view illustrating the bag and net being pulled through the incision.

DETAILED DESCRIPTION OF THE EMBODIMENTS

Figure 1:
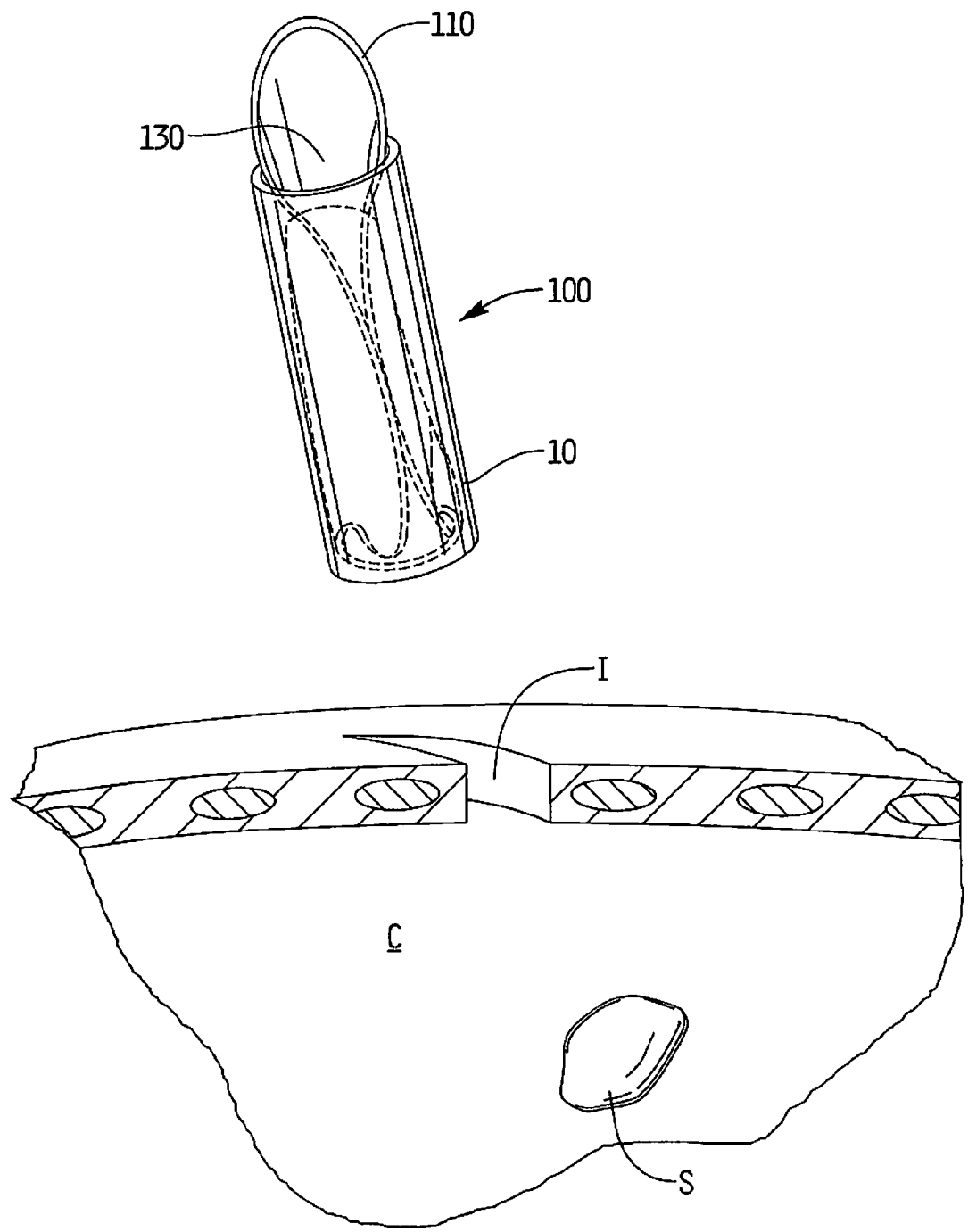
FIG. 1 is a perspective view of the retrieval bag of the specimen retrieval apparatus of the present disclosure in the collapsed insertion position within a delivery tube and shown outside the body cavity.

Embodiments of the present disclosure will now be described in detail with reference to the drawings, in which like reference numerals designate identical or corresponding elements in each of the several views. As used herein, the term distal refers to the portion of the instrument which is further from the user while the term proximal refers to that portion of the instrument which is closer to the user.

The surgical retrieval apparatus disclosed herein may find use in any procedure where access to the interior of the body is limited to a relatively small incision, with or without the use of a cannula, as in minimally invasive procedures. The devices herein may find particular use in minimally invasive thoracic surgery where access to the thoracic cavity is through a space located between adjacent ribs known as the intercostal space.

Referring initially to FIGS. 1-4, a surgical retrieval apparatus 100 is illustrated. Surgical retrieval apparatus is preferably configured and dimensioned for use in minimally invasive surgical procedures (e.g. thoracic, laparoscopic, endoscopic procedures). Surgical retrieval apparatus 100 includes an elongated supporting member or rim 110 and a retrieval bag 130 supported by the rim 110. As seen in the open configuration of FIG. 4, the rim 110 has a substantially oval shape and is of sufficient size so that a first portion, i.e. distal portion 115, is positioned within the body cavity C while a second portion, i.e. proximal portion 114, is positioned external to the cavity C. Similarly, the bag 130 is of a sufficient size to receive a tissue specimen in a first portion within the body cavity C, while a second portion extends outside the body cavity C to be grasped by the user. The rim 110 can be composed of shape memory material with a shape memorized expanded position. Alternatively, it can be composed of other materials which enable collapse/compression of the rim for insertion and expansion for placement within the body cavity, such as materials exhibiting spring-like characteristics.

Figure 4:
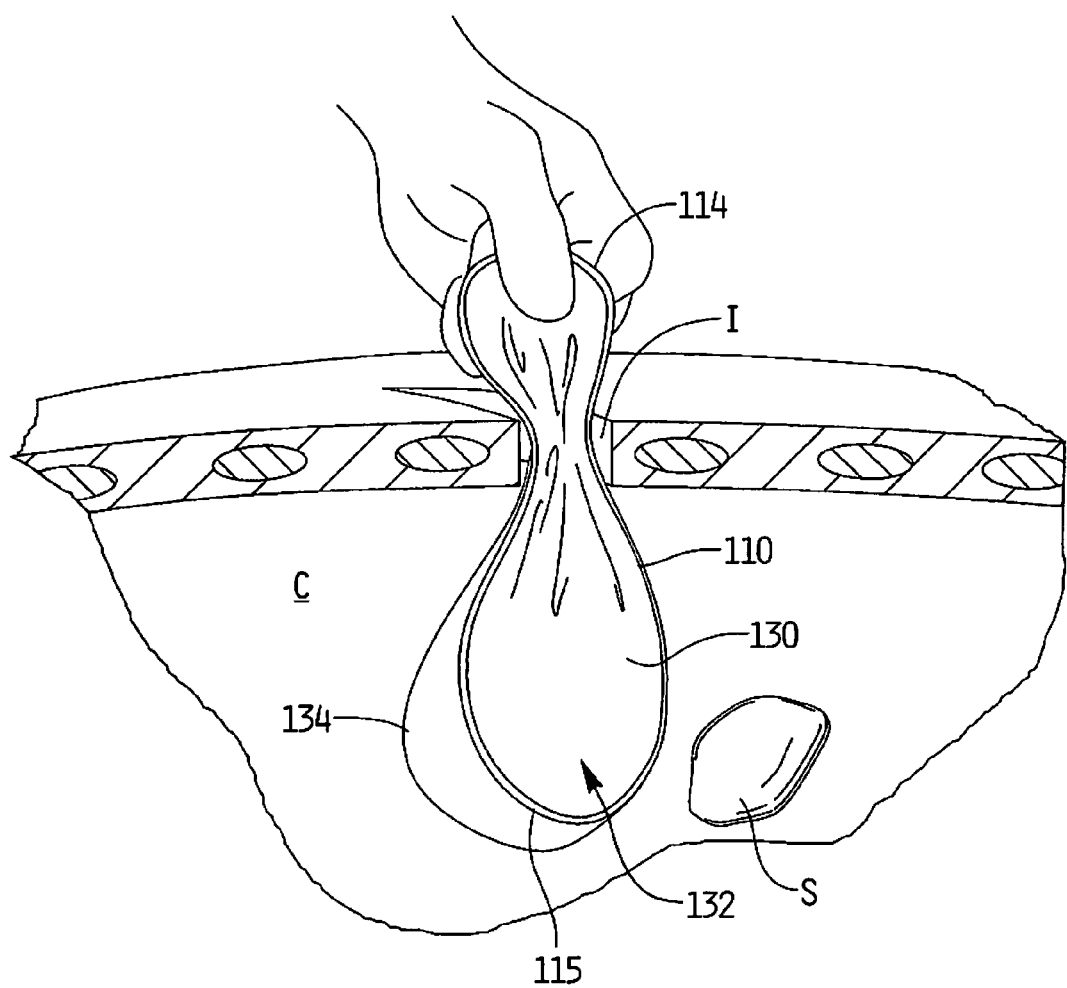
FIG. 4 is a perspective view illustrating the user grasping the proximal portion of the retrieval bag after removal of the delivery tube.

The retrieval bag 130 is shown in FIG. 4 in the open position. Once inserted inside the cavity C, expansion of the rim 110 expands the opening 132 of bag 130 due to the attachment of the bag 130 to the rim 110. Opening 132 of bag 130 is oriented transverse to an insertion axis (transverse to a longitudinal axis of the incision) so that it is angled toward the tissue specimen S. That is, the opening 132 faces the tissue specimen S. The closed opposite end of the bag is designated by reference numeral 134. The bag is preferably of sufficient size that it may be partially or fully inserted, depending on the size of the cavity. Additionally, being of a size that the rim extends outside the cavity to be grasped by the user, the user can always insert or retract the bag however much bag is introduced.

In use, the rim 110 and retrieval bag 130 can be delivered in a collapsed (e.g. folded) configuration through a delivery device 10 such as the configuration shown in FIG. 1. As can be appreciated, by delivering the bag 130 in the collapsed configuration directly through a delivery tube 10 (without an external sleeve as part of the device positioned over the bag), the overall profile of the apparatus is minimized which enables a smaller diameter access port or delivery member to be utilized.

The steps in the method of use of the surgical apparatus will now be described. In addition to the retrieval apparatus 100 having the support member 110 and retrieval bag 130, a surgical grasper and a retrieval net are also utilized in the procedure. In one embodiment, the net can be composed of a polymer mesh, although other materials are also contemplated.

Figure 2:
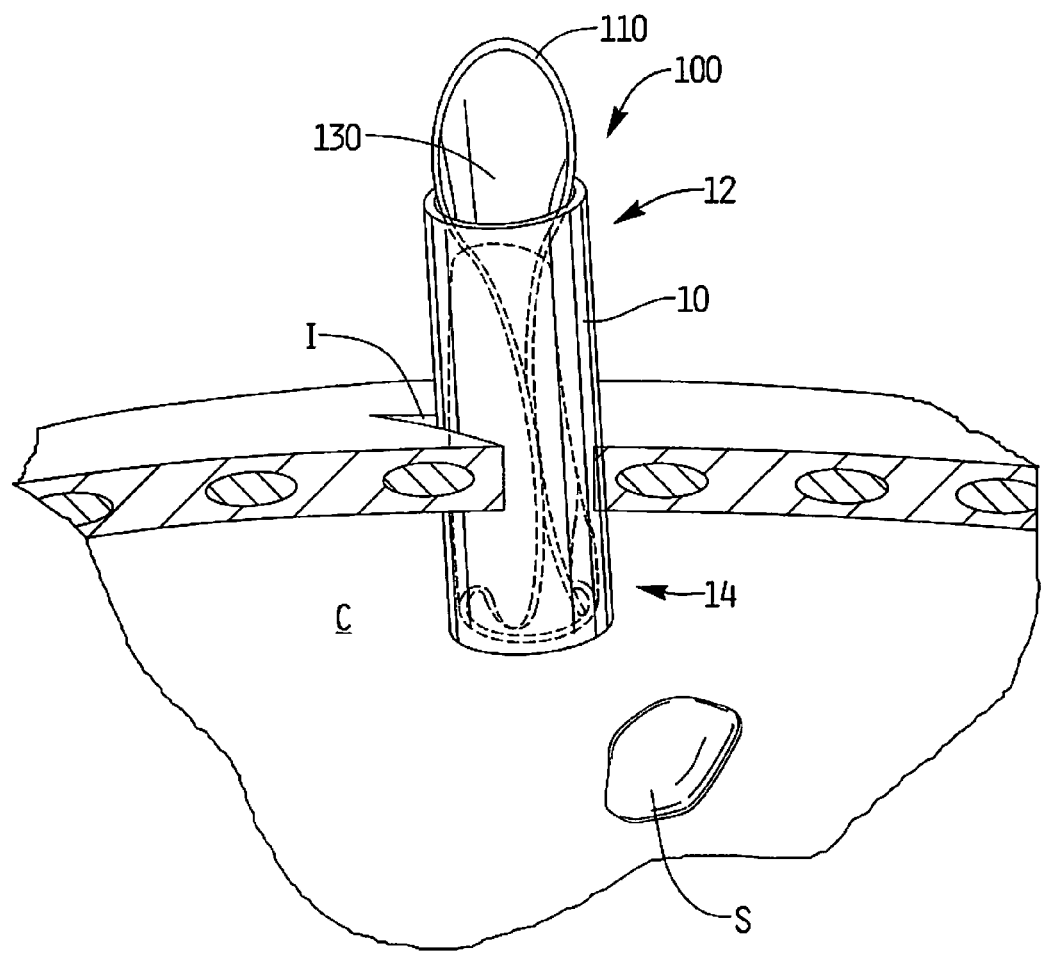
FIG. 2 is perspective view of the delivery tube and specimen retrieval apparatus of the present disclosure being inserted through an incision into the body cavity.
Figure 3:
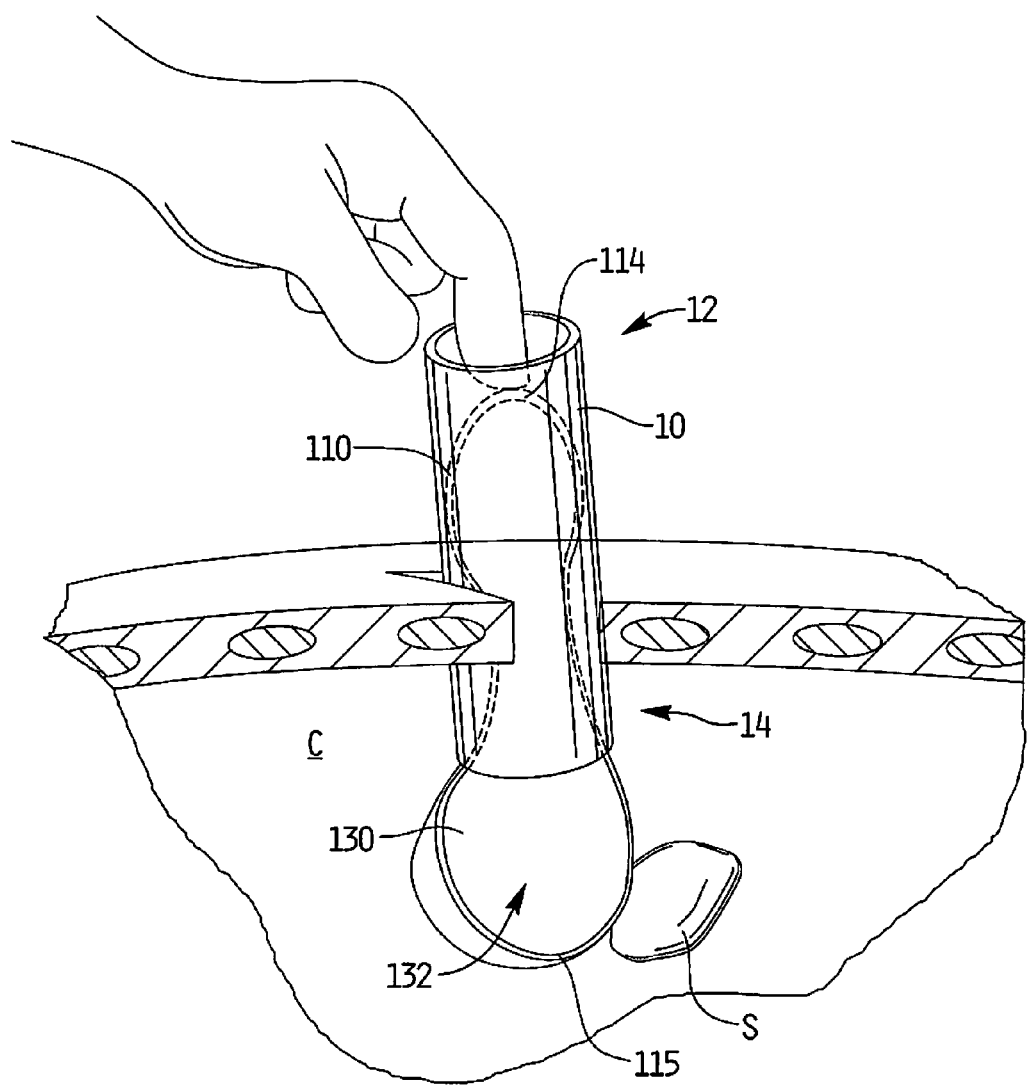
FIG. 3 is a perspective view of the retrieval bag being advanced by the user through the delivery tube.

In the first step, delivery tube 10, containing the apparatus 100 in the collapsed or folded position, is placed through the incision I as shown in FIG. 2, with the proximal portion 12 of delivery tube 10 extending outside the incision I and body cavity C and the distal portion 14 extending into the body cavity C. Next, the apparatus 100 is advanced from the delivery tube 10 by the surgeons finger(s) (FIG. 3) or alternatively by a pusher device pushing against a proximal portion 114 of rim 110 and/or bag 130. Once a portion of the rim 110 is advanced, e.g. distal portion 115, from the delivery tube 10, it automatically expands towards its normal larger configuration, thereby expanding bag 130. Once the apparatus 100 is partially advanced, the delivery tube 10 is withdrawn, enabling the remaining proximal portion 114 of the rim 110 and attached bag 130 to expand as it is free from the confines of the wall of the delivery tube 10. This expansion of the proximal portion 114 maintains this portion external of the incision I, as shown in FIG. 4, as its larger dimension cannot slide through the incision I. It is also held by the user. After withdrawal of the delivery tube 10, as can be appreciated, the rim 110 expands to thereby expand opening 132 of the bag 130 to present a large opening for the tissue specimen S. Note that the bag opening 132 is oriented toward the specimen. Also, in some embodiments the bag 130 can be oversized, so that it can be inserted to fill the cavity and the tissue sample S can simply be slid over the rim 110 into the bag 130 if desired.

Figure 5:
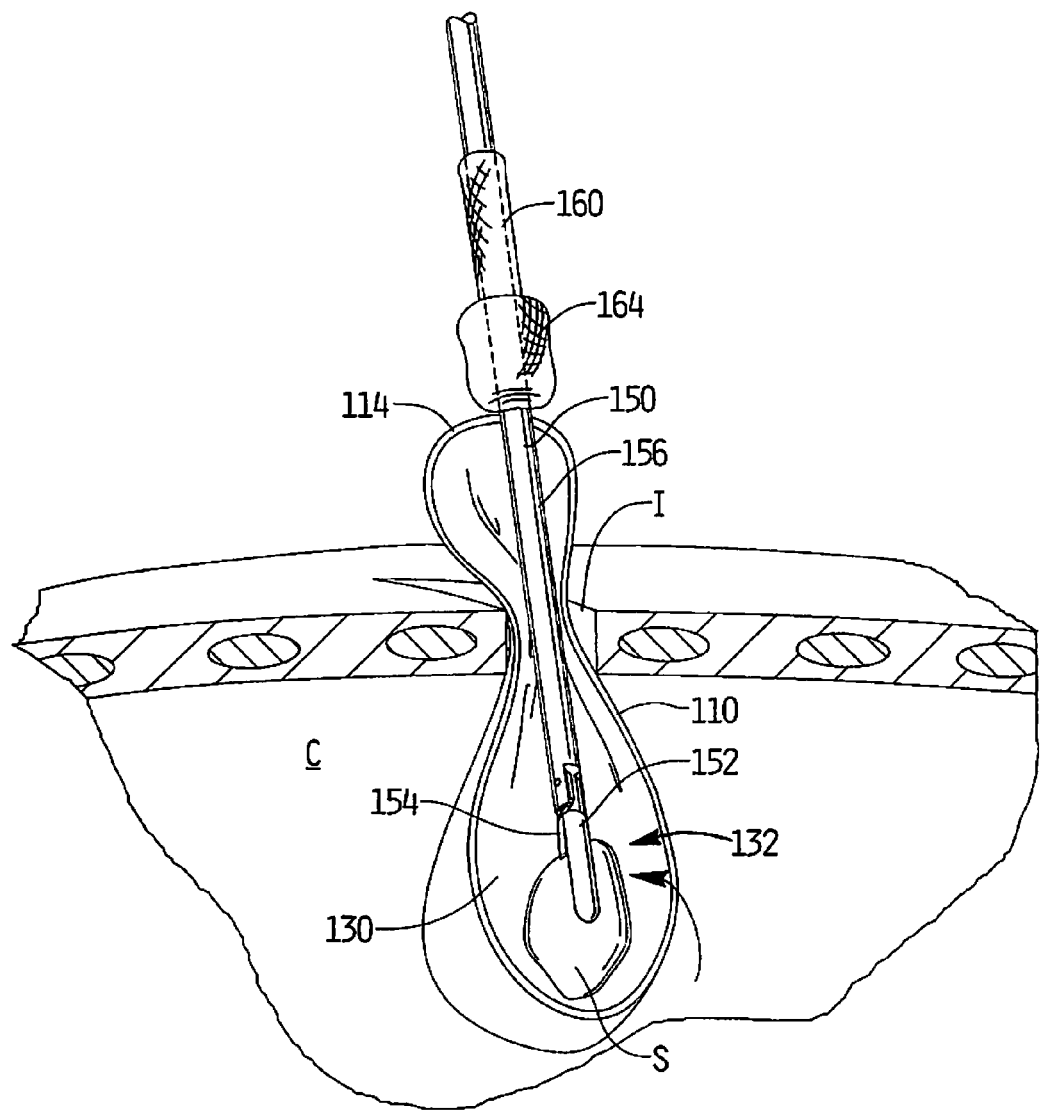
FIG. 5 is a perspective view illustrating a grasper with a net positioned thereon being inserted through the retrieval bag to grasp the tissue specimen and place it in the retrieval bag.

In the next step of the procedure, a grasper 150 (FIG. 5) is inserted through the incision I within the retrieval bag 130. The grasper 150 has a pair of jaws 152, 154 extending from shaft 156 which are movable between open and closed positions to grasp the specimen S within cavity C and place it through the opening 132 into the bag 130. The grasper 150 can also be utilized to maneuver the bag 130 over the specimen S. The grasper 150 also includes a net 160 positioned about (external) its shaft 156. A portion 164 of the net 160 is everted. The net 160 has an elongated shape with a diameter smaller than the diameter of the tissue specimen S intended to be removed. In this manner, when the specimen S is placed within the net 160, it is compressed which facilitates removal as will be discussed in detail below. The net can be composed of a polymeric material, although other materials are also contemplated. For example, it can be formed of a molded plastic.

Figure 6:
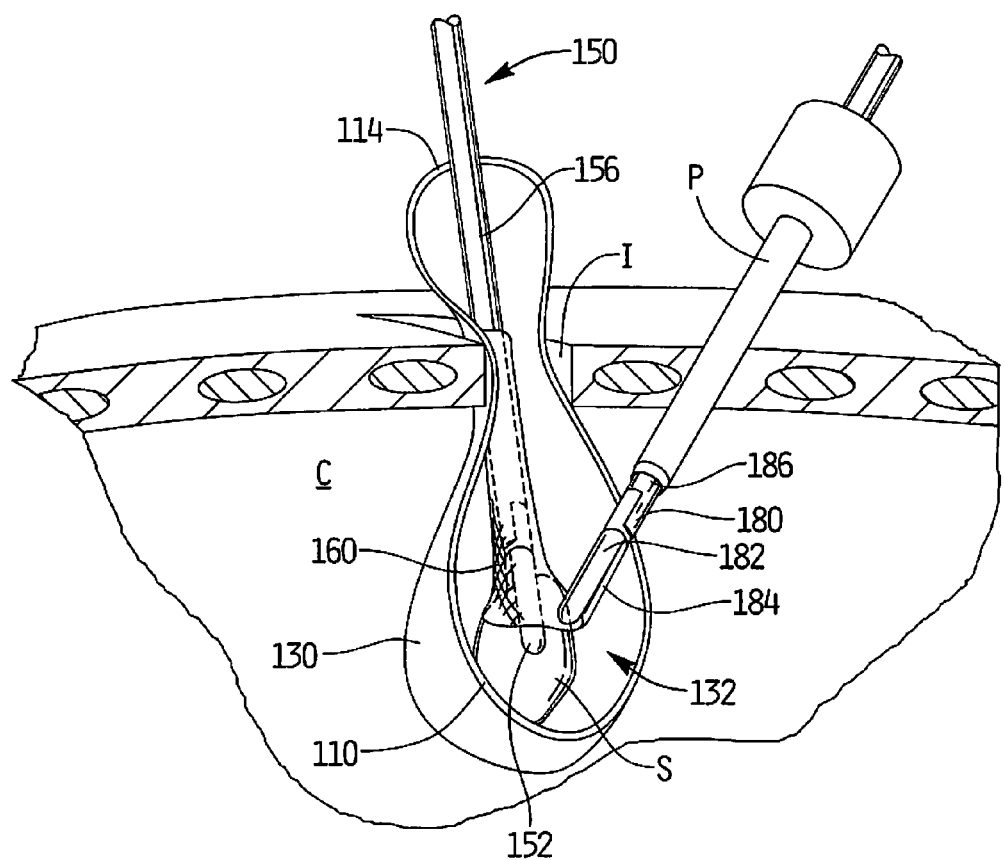
FIG. 6 is a perspective view illustrating a second grasper being inserted through a port extending through a second incision to unroll the net over the tissue specimen.

After placement of the specimen S in the bag 130, a second grasper 180 is inserted through a port P extending through a second incision as shown in FIG. 6. The grasper 180 has a pair of movable jaws 182, 184 extending from shaft 186. The grasper jaws 182, 184 are inserted through the opening 132 in the bag 130 to grasp the net 160 on grasper 150 and maneuver the net 160 over the specimen S. More specifically, after the net 160 has been pushed down along shaft 156 of grasper 150 so it is positioned within the distal region of the bag 130, the jaws 182, 184 grasp the rolled (everted) portion of the net 160 and pull it over the specimen S. The grasper 180 preferably places the net 160 over the entire specimen S which tightly holds the specimen, and can compress the specimen S to maintain it in an elongated shape, and prevent it from slipping to the bottom of the net during removal. Thus, the net functions to grip the tissue specimen spreading the force needed to withdraw it over a large area, while also allowing the specimen to conform to the shape to the incision. The net preferably has a space at the distalmost end to distend to prevent the tissue specimen from reaching the bottom of the bag and balling up. Once retained by the net 160, grasper 150 is removed from incision I. The second grasper 180 can also be removed through the second incision at this time or removed after the specimen S is removed. Note that the net preferably draws the specimen up into it as it is placed over the specimen to hold it therein.

Figure 7:
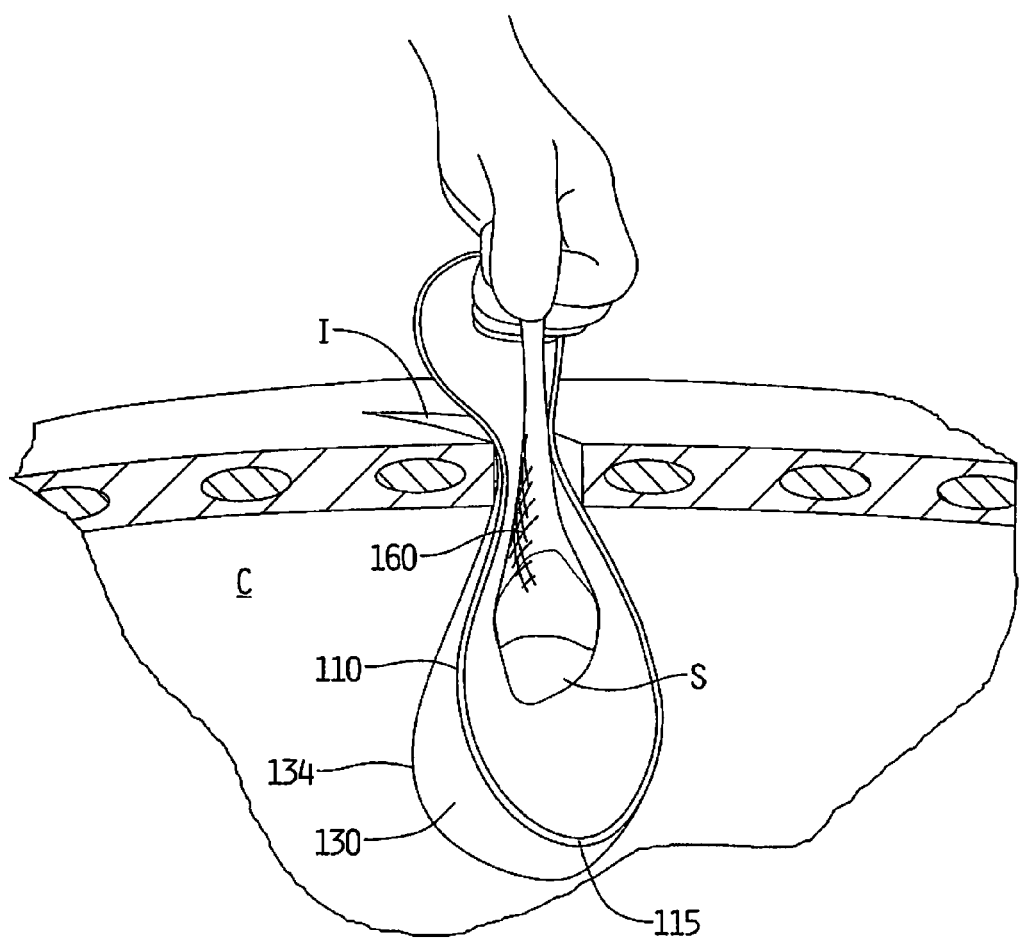
FIG. 7 is a perspective view illustrating the user grasping the proximal portion of the net to begin to pull the net through the incision.

As shown in FIG. 7, once the specimen S is retained within net 160, the user grasps the proximal portion of the net 160 and retracts it toward the incision I. The net 160 can operate in a "Chinese finger" fashion so that applying a proximal retraction force on the net 160 elongates the net and applies additional compression force on the specimen S. Once the specimen S is firmly held within the net 160, the net 160 and bag 130 are grasped by the user and removed through the incision I as shown in FIG. 8. Note that for removal the distal portion 115 of the rim 110 can be rotated to change the orientation of the bag opening 132 so the opening 132 faces toward the incision I instead of facing transversely, thereby the closed end 134 of the bag 130 would support or protect the specimen during removal.

Note the specimen can be maintained such that its long axis is substantially parallel to the incision which reduces the force required for removal through the incision or port. Also, as can be appreciated, the orientation and shape of the specimen S is substantially maintained to facilitate not only removal but pathology. Moreover, any compression or stretching of the specimen prior to removal occurs inside the bag which minimizes the risk of seeding.

Note also that the tissue specimen bags before containment so the risk of seeding is minimized. Also, since the net is taking the load, not the retrieval bag, the bag can be made of a thinner and lighter weight material and can be made more transparent.

As can be appreciated, the patient's body and cavity are shown schematically, it being understood that the surgical retrieval apparatus of the present disclosure can be used in the thoracic cavity, the abdominal cavity and other areas of the body for minimally invasive surgery.

A lubricious coating can be placed on the external surface of the specimen retrieval bags described herein to facilitate removal through the port or incision.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A method of retrieving a tissue specimen comprising:
   inserting a surgical retrieval apparatus through an opening in a patient's skin, the surgical retrieval apparatus including: a support member, and a retrieval bag extending from the support member and having an opening to receive the tissue specimen;
   placing a net over the tissue specimen;
   introducing the net into the retrieval bag, wherein the net is positioned on a shaft of a first grasper; and
   removing the net and retrieval bag from the patient's body to remove the tissue specimen.

2. The method of claim 1, further comprising advancing a second grasper into the retrieval bag.

3. The method of claim 2, wherein advancing the second grasper comprises advancing the second grasper through a second opening in the patient's skin.

4. The method of claim 3, further comprising grasping the net with the second grasper to place the net over the tissue specimen.

5. The method of claim 2, wherein the retrieval bag is positioned within a body cavity with the opening of the bag facing transversely with respect to an incision on the patient.

6. The method of claim 5, wherein the second grasper is inserted through the transversely positioned opening of the bag.

7. The method of claim 1, wherein the net has a diameter less than a diameter of the tissue specimen to grip the tissue specimen and maintain its position during removal.

8. The method of claim 1, wherein the retrieval bag is inserted in a collapsed position contained within a delivery tube.

9. The method of claim 1, further comprising withdrawing the first grasper prior to withdrawing the net from the incision.

10. The method of claim 1, further comprising applying a proximal force on the net to further apply a compressive force on the tissue specimen.

11. The method of claim 1, wherein inserting the surgical retrieval apparatus includes inserting the surgical retrieval apparatus into a thoracic cavity.

12. A method of retrieving a tissue specimen comprising:
   inserting a surgical retrieval apparatus through an opening in a patient's skin, the surgical retrieval apparatus including: a support member, and a retrieval bag extending from the support member and having an opening to receive the tissue specimen;
   unrolling a net from a shaft of a first grasper;
   introducing the net into the retrieval bag;
   placing the net over the tissue specimen after the net is introduced into the retrieval bag; and
   removing the net and retrieval bag from the opening in the patient's skin to remove the tissue specimen.

13. The method of claim 12, wherein the net is unrolled by a second grasper.

14. A method of retrieving a tissue specimen comprising:
   inserting a surgical retrieval apparatus through an opening in a patient's skin, the surgical retrieval apparatus including: a support member, and a retrieval bag extending from the support member and having an opening extending along its length to receive the tissue specimen, the opening of the retrieval bag extending from a position external of the opening through the skin to a position internal of the opening;
   placing a net over the tissue specimen; and
   removing the net and retrieval bag from the opening in the patient's skin to remove the tissue specimen.

15. A method of retrieving a tissue specimen comprising:
   inserting a surgical retrieval apparatus through an opening in a patient's skin, the surgical retrieval apparatus including: a support member, and a retrieval bag extending from the support member and having an opening to receive the tissue specimen;
   placing a net over the tissue specimen;
   introducing the net at least partially into the retrieval bag, wherein the net is positioned on a shaft of a first grasper; and removing the net and retrieval bag from the opening in the patient's skin to remove the tissue specimen.

16. A method of retrieving a tissue specimen comprising:

inserting a surgical retrieval apparatus through an opening in a patient's skin, the surgical retrieval apparatus including: a support member, and a retrieval bag extending from the support member and having an opening to receive the tissue specimen;

unrolling a net from a shaft of a first grasper;

introducing the net at least partially into the retrieval bag;

placing the net over the tissue specimen after the net is introduced into the retrieval bag; and removing the net and retrieval bag from the opening in the patient's skin to remove the tissue specimen.

* * * * *